United States Patent [19]

Knighton

[11] Patent Number: 4,571,244
[45] Date of Patent: Feb. 18, 1986

[54] SYSTEM FOR REMOVING GAS BUBBLES FROM LIQUIDS

[75] Inventor: David R. Knighton, San Francisco, Calif.

[73] Assignee: Biogenesis, Inc., San Francisco, Calif.

[21] Appl. No.: 607,370

[22] Filed: May 7, 1984

[51] Int. Cl.⁴ .............................................. A01M 5/16
[52] U.S. Cl. .................................... 604/118; 604/126; 128/672; 210/446
[58] Field of Search ................. 604/126, 122, 118, 53; 128/672; 55/159, 324; 210/446

[56] References Cited

U.S. PATENT DOCUMENTS

| | | | |
|---|---|---|---|
| 3,435,819 | 4/1969 | Reynolds et al. | 604/118 X |
| 3,590,818 | 7/1971 | Lemole | 604/118 X |
| 3,631,654 | 1/1972 | Riely et al. | 210/446 X |
| 4,031,891 | 6/1977 | Jess | 604/126 |

Primary Examiner—Stephen C. Pellegrino
Attorney, Agent, or Firm—Townsend and Townsend

[57] ABSTRACT

This invention provides a system for eliminating gas bubbles from a liquid. The liquid enters a chamber through an inlet port. The chamber has two outlet ports, the first bounded by a hydrophilic filter which passes liquid but not gas, and the second bounded by a hydrophobic filter which passes gas but not liquid. Entrapped gas bubbles entering the chamber pass through the hydrophobic filter to the atmosphere. The degassed liquid passes through the hydrophilic filter into tubing leading to the desired receptacle. This apparatus and method are particularly suitable for intravenous infusions and other medical applications in which the degassed liquid passes directly into the blood vessels of a patient.

4 Claims, 2 Drawing Figures

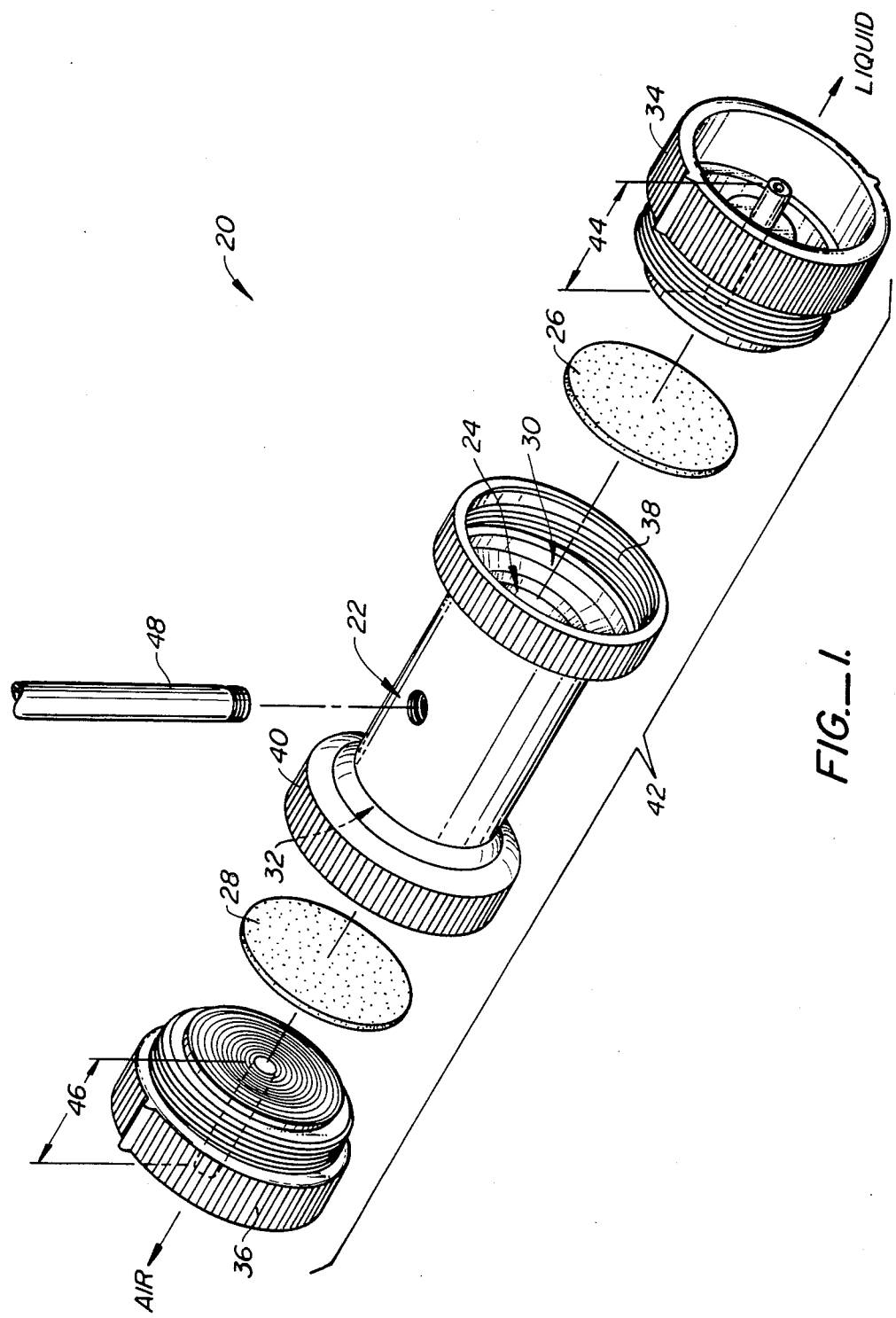

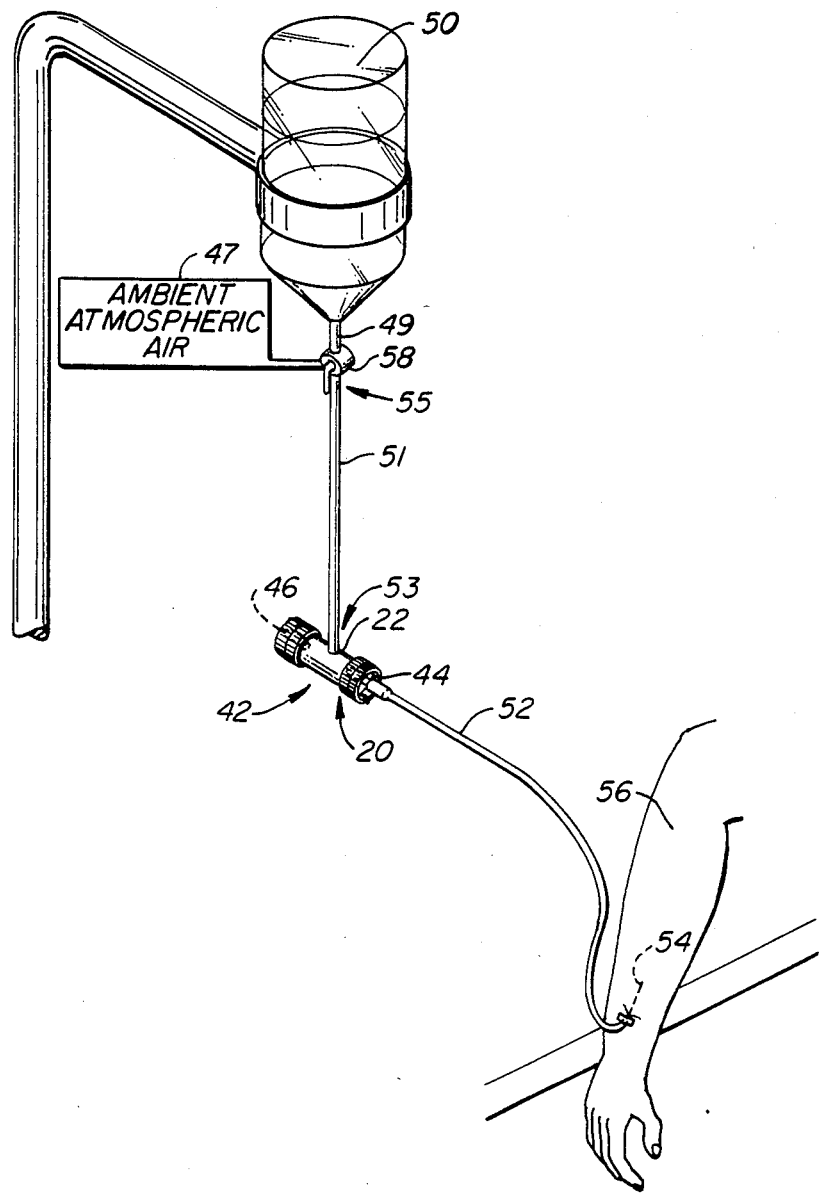
FIG._2.

SYSTEM FOR REMOVING GAS BUBBLES FROM LIQUIDS

BACKGROUND OF THE INVENTION

1. Field of the Invention

This invention relates generally to systems for removing gas bubbles from liquids, and more particularly to systems for removing gas or air bubbles from liquids intended for introduction into the bloodstream of a patient.

2. Description of the Prior Art

In medicine, the elimination of gas bubbles from a liquid to be injected into a patient's bloodstream is of great clinical importance. Many patients annually receive fluids from intravenous (IV) infusion devices connected through a catheter to a blood vessel. Additionally, medical practitioners are making greater use of arterial sensing devices which are introduced directly into the bloodstream, which devices can also introduce gas bubbles.

A bubble of gas, usually air, that may be trapped in the liquid is potentially dangerous to the patient. This air bubble can cause a gas or air embolism, which can obstruct blood circulation and perhaps cause an infarction, thereby cutting off blood circulation. As little as 0.1 ml of gas in an arterial line can be dangerous—even fatal—to an adult human.

One method for dealing with this problem is for standard IV infusion bottles to be held in a vertical position, for bubbles to rise to the top; this is common practice.

Additionally, hydrophilic filters are used in-line in intravenous infusion devices, between the IV supply source and the patent. A hydrophilic filter permits passage of the liquid but prevents the passage of gas bubbles into the IV feed line. The hydrophilic filter is housed in a conventional "dripmeter", such as the "Millipore ®IVEX-H.P. Filterset", No. 4524, manufactured by Abbott Laboratories of North Chicago, Ill.

However, a gas or air bubble of sufficient size will block the passage of liquid into the patient, necessitating the discarding of the commonly used drip device connected to the feed line and the starting of the infusion anew. Also, it is difficult to visually detect when liquid flow has stopped due to blockage, because the dripmeter will look the same when it is either completely full of air or liquid, both of which are typically clear.

Other apparatus such as arterial sensing devices are currently purged of air bubbles after drawing blood, and must be monitored by careful visual inspection. No device assures that gas or air bubbles have been forced out of the patient liquid supply line.

STATEMENT OF OBJECTS OF THE INVENTION

An object of this invention is to provide a gas bubble trap system which is particularly useful in IV infusions. Liquid from an IV fluid supply flows into a chamber having two filters.

The first filter is hydrophilic; it will not allow gas bubbles to pass through, but will allow liquid to pass through. The second filter is hydrophobic and allows air to pass out from the chamber but will not pass liquid. The gas-free liquid passes through the hydrophilic filter and flows into the patient.

The system is inexpensive and simple to use. A nurse or doctor merely inserts the device into the IV line. Entrapped gas flows out of the chamber through the second gas-passing filter, the gas-free fluid flows through the first fluid-passing filter into the patient.

Another object of this invention is to use a hydrophilic filter to pass liquid at a rate sufficient for the nutritional and other liquid needs of the patient.

Another object of the invention is to provide a device which removes gas bubbles from a liquid, including filters designed to resist the hydrostatic pressure of the liquid caused by pumping or gravitational flow. The pressure forces the liquid through a hydrophilic first filter which is substantially impermeable to gas bubbles. The pressure also forces any entrapped gas through a hydrophobic second filter which is substantially impermeable to liquids.

Still another object of the invention is to provide a device which, in the case of failure, will not endanger the patent.

SUMMARY OF THE INVENTION

This invention provides a system for removing gas bubbles from a liquid. The system includes a chamber having an inlet port for receiving the liquid, a first outlet port for expelling the liquid, and a second outlet port for expelling the gas bubbles.

A first filter, comprised of a hydrophilic material, seals the first outlet port. A second filter, comprised of a hydrophobic material, seals the second outlet port. This arrangement ensures that substantially all of the liquid entering the chamber will exit the chamber through the first outlet port substantially free of the gas bubbles.

Of particular interest is that this inventive system provides apparatus and method for supplying intravenous liquids free of gas bubbles, and particularly air bubbles, to a patient via a tube and catheter.

Additionally, this invention provides a system for selectively and alternately either (1) measuring central venous pressure of a patient or (2) introducing a liquid substantially free of gas, particularly air, bubbles into the venous system of a patient. The system includes a liquid supply and a manometer having first and second ends.

A filtering device is connected between the first end of the manometer and the patient. The filtering device has a chamber having (1) a hydrophilic filter for passing liquid but not air bubbles to the patient, and (2) a hydrophobic filter for passing air but not liquid out of the chamber and away from the patient.

Also included is a selector valve, having first and second open positions. The first position places ambient atmospheric air into communication with the second end of the manometer, to permit measurement of central venous pressure of the patient. The second position places a liquid supply in communication with the second end of the manometer, to supply liquid free of gas bubbles to the patient.

The system also includes a hydrophobic filter having a hydrostatic burst pressure lower than that of the hydrophilic filter.

This invention offers several advantages over previous approaches. First, no guess work is used in deciding whether or not gas bubbles are passed to the patient; the hydrophobic-hydrophilic filter interactive system ensures that only liquids substantially free of gas passes through the hydrophilic filter to the patient. Second, gas bubbles are automatically captured by the hydrophilic filter, and migrate toward and through the hydrophobic filter to the atmosphere.

Third, by looking through the various transparent tubes included within this system, it can be determined with a glance whether or not the fluid is flowing as it should be. Fourth, intravenous pressure can be checked at any time, when the overall system includes an IV liquid supply for a patient, by simply admitting ambient atmospheric air into the manometer, permitting the liquid to seek its own level to thereby provide a reading of the patient's central venous pressure. Then, liquid flow can be immediately resumed by returning the selector valve to its liquid flowing second position.

BRIEF DESCRIPTION OF THE DRAWINGS

FIG. 1 is an exploded view of the inventive device showing the inlet port, filters, and gas bubble and liquid outlet ports; and FIG. 2 is a diagrammatic representation of the arm of a patient receiving fluid intravenously with the IV tubing plugged into the inventive device, and the liquid exit port of the device attached through a catheter to the patient.

DESCRIPTION OF THE SPECIFIC EMBODIMENTS

With reference to FIG. 1, the inventive devioe, hereinafter referred to as the "debubbler", is indicated at 20. The debubbler is comprised of an inlet port 22 opening into a hollow chamber 24. The chamber is bounded by hydrophilic filter 26 and hydrophobic filter 28. Filter 26 is made of hydrophobic material which will pass liquid but not gas. Filter 28 will pass gas but not liquid.

Filters 26, 28 are placed against the mouths 30 and 32 of the chamber, and are held snugly in place by respective threaded filter holders 34 and 36. To receive threaded filter holders 34, 36, the chamber 24 terminates with respective internally threaded lips 38, 40. When all parts are assembled, they define a cylinder 42.

A tube 48 connects cylinder 42 to a liquid supply (not shown). Filter holder 34 is provided with a first outlet port 44 through which liquid can flow; the opposite holder 36 has a gas outlet port 46 through which gas can pass.

One improvement offered by this invention is the use of dual filters, one of which will pass liquid but not gas, the other which will pass gas but not liquid. Properties of these filters are described below.

Hydrophobic membranes are well-known in the art and are commercially available. DURAPORE TM hydrophobic membranes with a 0.45μ pore size, manufactured by Millipore (Cat. #HVHP04700) are satisfactory. It is desirable that pore size of the filter be maintained at less than 0.5μ when the debubbler is used for medical purposes, because the filter will then be bacteriostatic. This means that bacteria will be unable to enter the debubbler through lhe filter 28.

Hydrophilio membranes are also well known in the art. DURAPORE TM and NUCLEOPORE TM have hydrophilic filters which are satisfactory. Again, pore sizes of less than 0.5μ are preferred to prevent bacteria that might be in the debubbler from entering a patient.

FIG. 2 shows debubbler 20 in a typical use. Liquid flows from an IV liquid supply bottle 50 into the debubbler 20 through tube 48 under the force of gravity. According to this aspect of the invention, the system provides for selectively and alternately either (1) measuring central venous pressure of a patient or (2) introducing a liquid substantially free of gas, particularly air, bubbles into the venous system of a patient. The system includes a source of ambient atmospheric air indicated at 47, a liquid supply such as IV bottle 50, and a manometer 51 with a scale (not shown) for reading central venous pressure, the manometer having first end 53 and second end 55.

Cylinder 42 provides a means for filtering which is connected between the first end 53 of manometer 51 and the patient. As described above, cylinder 42 has a chamber 24 having (1) a hydrophilic filter (not shown in FIG. 2) for passing liquid but not air bubbles to the patient, and (2) a hydrophobic filter (not shown in FIG. 2) for passing air but not liquid out of the chamber and away from the patient.

Also included is a selector valve 58, having first and second open positions (not shown). Selector valve 58 is mounted on second end 55 of manometer 51, and connected through conduit 49 to IV bottle 50. The first position places atmospheric air from 47 into communication with second end 55 of manometer 51, to permit measurement of central venous pressure of the patient by reading the manometer scale. The second position places a liquid supply such as IV bottle 50 in communication with second end 55 of the manometer, to supply liquid which is free of gas bubbles to the patient.

Air and other entrapped gas bubbles in the IV liquid flow into debubbler 20. By the pressure of the fluid column primarily in manometer 51, the gas bubbles are forced out into the atmosphere through gas bubble outlet port 46 which is bounded by the hydrophobic filter.

Liquid without gas bubbles is forced through liquid outlet port 44 and enters line 52 which is connected to a catheter 54 inserted into a blood vessel in for example an arm 56 of a patient (not shown).

Another advantage of this dual hydrophilichydrophobic filter system is that air bubbles entering chamber 24 of cylinder 42 cannot accumulate to block liquid flow through the hydrophilic filter and its associated port 44. Liquid flows into the patient continuously. In previous systems using only hydrophilic filters, a gas or air bubble of sufficient size blocks the flow of liquid into a patient, necessitating discarding the filters and starting anew.

The filters which are commercially available can withstand bubble pressures equivalent to hydrostatic head pressures of 34 feet of water or more depending upon filter pore size. Normally, the gravity flow IV bottle 50 is positioned less than 10 feet, and usually less than 6 feet, above the level of the patient.

Under normal oiroumstanoes, the liquid height in manometer 51 is not oapable of bursting the filters to make the system inoperative. Debubbler 20 is thus ideally adaptable for use with the IV systems. The pressure resistance of the hydrophilic filter is an important consideration if the liquid is actively pumped under increased pressure into the debubbling device.

During introduction of the IV liquid into the patient, it is more important to prevent gas bubbles from entering the patient than it is to prevent liquid from escaping through the gas outlet 46. Thus, if pressure increases in chamber 24 toward an upper threshold beyond which gas bubbles are forced through the hydrophilic filter into the patient, the hydrophobic filter is preferably selected to burst before the pressure exceeds this upper threshold, or before the hydrophilic filter bursts.

Proper respective burst pressure selection causes the liquid to flow harmlessly out through the now burst hydrophobic filter and open gas outlet 46. Appropriate choice of filter bursting limits can incorporate this safety feature, which is another advantage of this invention over previous systems.

In a scenario in which the hydrophilic filter bursts but the hydrophobic filter holds, the result will be no worse than in a conventional IV system, because liquid and any entrapped gas will flow through the liquid outlet port 44; the system will operate like a conventional IV system. Some gas will exit through the still intact port 46, depending upon the hydrostatic pressure. Thus, a level of safety still exists for the patient.

As is known according to the laws of chemistry and physics, increasing the hydrostatic pressure will increase the amount of gas dissolved in the IV liquid. Dissolved gas will pass with the liquid through the hydrophilic filter. While this poses a theoretical danger to a patient, analogous to "the bends" experienced by divers, there is no real danger in a clinical setting. This is because the hydrostatic pressure is so low that the quantity of dissolved gas molecules entering the patient will be far too small to create the possibility of physiological damage.

Another possible concern arises as the fluid level settles toward zero in the IV bottle 50, suggesting fluid flow might reverse, i.e., blood might flow in reverse out of the patient.

However, in a conventional IV system, it is known that the back-pressure from the patient's blood vessel becomes equal and opposite to the pressure in the IV flow system (i.e., tube 48 and line 52) leading to the blood vessel. In an IV system incorporating debubbler 20, the result is identical. Because of this equilibrium, the final few drops of IV liquid remain in the IV flow system. There is no negative or vacuum pressure to cause the system to drain blood from the patient. Thus, there is no danger than negative pressure will cause a reverse blood flow from the patient lo debubbler 20.

EXAMPLE

In an experimental apparatus using the FIG. 2 assembly, NUCLEOPORE TM hydrophilic filters of pore sizes 1.0μ and 0.45μ were tested. Using circular hydrophilic filters 26 of 13 mm diameter, liquid flow rate through the 1.0μ pore-sized filter was 24 liters per hour. The liquid flow rate through the 0.45μ pore-size filter was 6 liters per hour. Both flow rates are adequate as they are far in excess of normal patient requirements. The data indicate that smaller pore sizes and/or filter diameters would be adequate for most clinical purposes.

The 13 mm diameter hydrophilic filter with pore size of 1.0μ can withstand a critical bubble pressure of about 15 p.s.i. (=34.7 feet water) before bursting. The 13 mm diameter hydrophilic filter with pore sizes of 0.45μ can withstand a critical pressure of 33 p.s.i. (=76.2 feet water). It is evident that smaller pore size not only confers desirable bacteriostatic properties to the debubbler 20, but also permits operation of the device at greater hydrostatic pressure.

It is desirable that the hydrophilic filter be minimally reactive. Tests show that about 0.1μ g of DNA, IGg or albumin may bind per $cm^2$ area of hydrophilic filter. While this insignificantly affects the liquid flow rate to the patient, it should be considered when determining the amount of desired liquid being infused into the patient.

The foregoing invention has been described in some detail by way of illustration and example for purposes of clarity and understanding, referring primarily to adapting the debubbler device for intravenous infusions. However, it will be obvious to those skilled in the art that the system can easily be adapted for other purposes whenever it is necessary to remove bubbles from a liquid. The scope of the invention is defined by the appended claims.

What is claimed is:

1. A system for selectively and alternately either measuring central venous pressure of a patient or introducing a liquid substantially free of gas bubbles into the venous system of a patient, the system comprising:
   (a) a liquid supply;
   (b) a manometer, having first and second ends;
   (c) a means for filtering, connected between the first end of the manometer and the patient, provided with a chamber having a hydrophilic filter for passing liquid but not gas bubbles to the patient, and a hydrophobic filter for passing gas bubbles but not liquid out of the chamber and away from the patient; and
   (d) a selector valve having first and second open positions, the first position placing ambient atmospheric air into communication with the second end of the manometer to permit measurement of central venous pressure of the patient, and the second position placing the liquid supply in communication with the second end of the manometer to supply liquid substantially free of gas bubbles to the patient.

2. A system for selectively and alternately either measuring central venous pressure of a patient or intravenously introducing a liquid containing gas bubbles into the body of the patient, the system comprising:
   (a) a manometer, having a measuring tube defining an upper end and a lower end;
   (b) a selector valve, connected to the upper end portion of the manometer tube, adjustable to first and second positions;
   (c) a liquid supply, connected to the selector valve, for supplying liquid to the manometer tube when the selector valve is in the first position; and
   (d) a chamber, connected between the lower end of the manometer and the patient, for alternately receiving from the manometer the liquid when the selector valve is in the first position and ambient atmospheric air when the selector valve is in the second position, the chamber including a hydrophilic filter which passes liquid but not gas and bubbles to the patient, and a hydrophobic filter which passes air but not liquid out of the chamber and away from the patient, so that the patient receives liquid substantially free of gas bubbles.

3. The system of claim 2, wherein the measuring tube of the manometer includes a graduated scale affixed to the manometer, and wherein the manometer is transparent so the liquid flow and liquid level can be observed by the human eye.

4. A method for selectively and alternately either measuring central venous pressure of a patient or intravenously introducing a liquid containing gas bubbles into the body of the patient, comprising the steps of:
   (a) supplying intravenous liquid containing air bubbles;
   (b) providing a manometer having first and second ends;

(c) connecting a filtering means between the first end of the manometer and the patient, the filtering means including a chamber, a hydrophilic filter for passing liquid but not air bubbles to the patient, and a hydrophobic filter for passing air but not liquid out of the chamber and away from the patient; and (d) connecting a selector valve, having first and second operating positions, to interconnect ambient atmospheric air, the liquid, and the manometer at the manometer's second end, such that the first position admits liquid for supply to the patient without gas bubbles, and the second position admits ambient atmospheric air to permit measuring the patient's central venous pressure.

* * * * *